(12) United States Patent
Ferenz et al.

(10) Patent No.: US 7,635,581 B2
(45) Date of Patent: Dec. 22, 2009

(54) PROCESS FOR PREPARING ORGANICALLY MODIFIED SILOXANES

(75) Inventors: Michael Ferenz, Essen (DE); Burghard Gruening, Essen (DE); Christian Hartung, Essen (DE); Oliver Thum, Ratingen (DE)

(73) Assignee: Goldschmidt GmbH, Essen (DE)

( * ) Notice: Subject to any disclaimer, the term of this patent is extended or adjusted under 35 U.S.C. 154(b) by 415 days.

(21) Appl. No.: 11/669,254

(22) Filed: Jan. 31, 2007

(65) Prior Publication Data

US 2007/0184006 A1    Aug. 9, 2007

(30) Foreign Application Priority Data

Feb. 4, 2006    (DE) .................... 10 2006 005 100

(51) Int. Cl.
*C12P 9/00* (2006.01)
*C12N 9/14* (2006.01)
*C12N 9/18* (2006.01)
*C08G 77/04* (2006.01)

(52) U.S. Cl. .................... 435/131; 435/195; 435/197; 525/479

(58) Field of Classification Search .................... None
See application file for complete search history.

(56) References Cited

U.S. PATENT DOCUMENTS

| 6,121,347 A | 9/2000 | Yatsuyanagi |
| 6,320,065 B1 | 11/2001 | Gruning et al. |
| 2003/0008917 A1 | 1/2003 | Brock et al. |
| 2003/0096919 A1 | 5/2003 | Ichinohe |
| 2007/0004891 A1 | 1/2007 | Ichinohe |
| 2009/0017519 A1* | 1/2009 | Thum et al. .................. 435/180 |

FOREIGN PATENT DOCUMENTS

| EP | 0407959 A | 1/1991 |
| EP | 0965645 A2 | 12/1999 |
| EP | 1250842 A1 | 10/2002 |
| JP | 08157601 A | 6/1996 |
| WO | WO-2004/099290 A | 11/2004 |

* cited by examiner

*Primary Examiner*—Herbert J. Lilling
(74) *Attorney, Agent, or Firm*—Frommer Lawrence & Haug LLP

(57) ABSTRACT

The invention provides a process for preparing siloxanes modified with organic esters, by hydrosilylating siloxanes with terminally unsaturated esters, which comprises preparing the terminally unsaturated esters used using at least one enzyme as catalyst.

11 Claims, No Drawings

PROCESS FOR PREPARING ORGANICALLY MODIFIED SILOXANES

This application claims benefit under 35 U.S.C. 119(a) of German patent application DE 10 2006 005 100.9, filed on 21 Feb. 2006.

Any foregoing applications including German patent application DE 10 2006 005 100.9, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

The invention relates to a new process for preparing siloxanes modified with organic groups.

Organically modified siloxanes are used in a wide variety of applications. Their properties can be tailored by the nature of the modification and also by the amount of modification.

One industrially utilized method to produce organically modified siloxanes is that of hydrosilylation. It involves reacting Si—H-functional siloxanes with terminally unsaturated organic reaction partners in the presence of transition metal catalysts.

For example, it is possible to use allyl polyethers to attach organophilic or nonionic hydrophilic groups to a siloxane backbone. Such compounds find their use, for example, as polyurethane foam stabilizers, as defoamers in fuels or as additives in paints and coatings.

In contrast, by reaction with α-olefins the siloxane is linked to hydrophobic groups. The resulting silicone waxes serve e.g. as additives in personal care applications.

It is apparent in numerous fields of application that the effect of the siloxane is dependent on the compatibility with the formulation in question. It is therefore desirable to be able to have recourse to a broad raw materials base of organic radicals which, moreover, reproducibly and with precision and very good yields, can be addition-reacted onto the silicone skeleton by hydrosilylation.

One very broad and favorably priced raw materials base is represented by the group of carboxylic acids. The products available are numerous and differ markedly in their properties. An example of this is the class of fatty acids.

Carboxylic acids can also be attached to the siloxane backbone in the form of their esters. Siloxanes of this kind, modified with organic ester groups, are obtainable via a variety of synthetic routes and find application, for example, as additives for toners.

It is possible for siloxanes carrying alcohol groups to be esterified or for carboxylic esters to be transesterified with siloxanes carrying alcohol groups.

These two methods presuppose, however, that a siloxane carrying alcohol group must be synthesized, which in many cases can be problematic. Siloxanes of this kind are obtainable through hydrosilylation of terminally unsaturated alcohols such as allyl alcohol or glycerol monoallyl ether, for example. The hydrosilylation, however, is generally accompanied by side reactions, in which the Si—H units react with the OH function to form SiOC groups. In the case of highly modified siloxanes, the reaction products rapidly undergo uncontrolled and unwanted crosslinking.

Moreover, the reaction of the obtained alcohol-functional siloxanes to form the corresponding esters is frequently problematic, since many of the reaction conditions typically employed for esterification or transesterification, such as the use of strong acids at temperatures of more than 100° C., lead to rearrangement reactions in the siloxane backbone.

A further route to obtain carboxylic ester functionalized siloxanes is the hydrosilylation of terminally unsaturated esters. Although patent applications JP-A-8157601 and US-A-2003/0096919 describe the use of terminally unsaturated esters, they give no information concerning the preparation and, optionally, purification of these compounds. Since, however, the hydrosilylation is a very sensitive reaction, extensive purification steps are needed in some cases in order to obtain esters which can be subjected without problems to further reaction with siloxanes. On economic and toxicological grounds a low catalyst concentration is desirable, typically below 15 ppm, as a result of which, however, a trouble-free reaction profile is even more difficult to achieve.

Conventional methods for industrial preparation of esters, of the kind frequently used in the preparation of cosmetic esters, for example, involve the use of acids or metal salts as catalysts.

However, terminally unsaturated esters which have been prepared by such standard methods, as for example by acid catalysis with para-toluenesulfonic acid or by metal salt catalysis, using tin(II) oxalate, for example, yield unsatisfactory results in hydrosilylation, if the catalysts used are separated off only by simple methods, such as neutralization and filtration. Examples 1, 2, 11 and 12, which are described later on, demonstrate this fact by means of experimental data.

Therefore, it was an object of the present invention to develop a process which first of all allows the simple preparation of terminally unsaturated organic esters, which subsequently can be linked to siloxanes by hydrosilylation without problems and without substantial workup steps.

Further objects, not specified explicitly, will become apparent from the context of the subsequent description, examples, and claims.

Surprisingly it has been found that organic esters which contain a terminal double bond can be subjected easily and in very good yields by hydrosilylation to addition reaction with siloxanes if the linking of the ester bond is accomplished by means of enzymatic catalysis.

The invention accordingly provides a process for preparing siloxanes modified with organic esters, which comprises biocatalytically preparing the terminally unsaturated esters of the general formula I $$W\underset{m}{\underbrace{\phantom{XX}}}\underset{n}{\underbrace{\overset{O}{\underset{\|}{C}}}}O\underset{o}{\underbrace{A}}\underset{p}{\underbrace{B}}\underset{q}{\underbrace{\overset{O}{\underset{\|}{C}}}}R_a \quad (I)$$

where

W is hydrogen or methyl (in one embodiment of the invention W is hydrogen), m is a number selected from the ranges consisting of 0 to 28 and 1 to 17, n is 0 or 1, o is 0 to 100, A is an oxyalkenyl radical of the general formula Ia

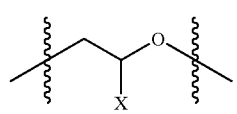

(Ia)

where
X radicals independently are identical or different radicals from the group —H, —$CH_3$, —$CH_2CH_3$ or -phenyl, (in one embodiment of the invention, X is hydrogen),
p is from 0 to 20,
B if p=1 is a glycerol-derived oxyalkenyl radical, optionally esterified with $R_b$, of the general formula Ib

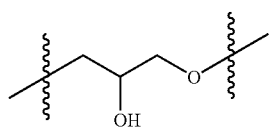

(Ib)

where
$R_b$ is the acyl radical of linear, branched, saturated or unsaturated carboxylic acids having 2 to 30 carbon atoms and optionally carrying additional hydroxyl groups, or
B if p=1 is the radical of the general formula Ic

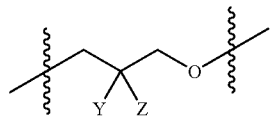

(Ic)

where
Y and Z independently of one another are identical or different radicals from the group —H, —$CH_3$, —$CH_2CH_3$, —$CH_2OH$ or —$CH_2OR_b$,
where
$R_b$ is defined as above, or
B if p≧2 is a polyglycerol radical formed from monomers of glycerol and optionally esterified with $R_b$,
$R_b$ is defined as above,
$R_a$ is hydrogen, $R_{a1}$ or $R_{a2}$,
where
$R_{a1}$ is a linear or branched, saturated or unsaturated alkyl radical having 1 to 200 carbon atoms which optionally carries hydroxyl groups, optionally carries hydroxyl groups esterified with carboxylic acids and optionally carries amino, alkylamino or dialkylamino groups, (in one embodiment of the invention, the alkyl radical has 1 to 50 carbon atoms or 1 to 4 carbon atoms and the alkyl of the alkylamino or dialkylamino groups have 1 to 4 carbon atoms)

$R_{a2}$ is a radical of the general formula Id

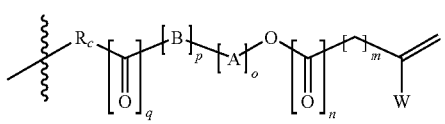

(Id)

and
$R_c$ is a saturated or unsaturated difunctional hydro-carbon radical having 2 to 20 carbon atoms, (in one embodiment of the invention the hydrocarbon radical has 10 to 18 carbon atoms)
where
q=0 or 1 provided that n+q=1, and
if $R_a$ is hydrogen, then q is 0 and o+p≧1.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Another embodiment of the invention are compounds of the general formula I wherein
n, o and p=0,
W is hydrogen,
m is a number selected from the ranges consisting of 0 to 28 and 1 to 4,
q is 1,
$R_a$, $R_{a1}$=$R_{a11}$ or $R_a$=$R_{a2}$.
$R_{a11}$ here is the alkyl radical derived from commercially customary acids, such as acetic acid, propanoic acid, butanoic acid, pentanoic acid, chloroacetic acid, trifluoroacetic acid, ethylhexanoic acid, isononanoic acid, isotridecanoic acid or isostearic acid.

Additionally, $R_{a11}$ is the alkyl radical derived from monobasic fatty acids based on natural vegetable or animal oils having 6 to 30 carbon atoms, in particular having 8 to 22 carbon atoms, such as caproic acid, caprylic acid, capric acid, lauric acid, myristic acid, palmitic acid, palmitoleic acid, isostearic acid, stearic acid, 12-hydroxystearic acid, dihydroxystearic acid, oleic acid, linoleic acid, petroselenic acid, elaidic acid, arachidic acid, behenic acid, erucic acid, gadoleic acid, linolenic acid, eicosapentaenoic acid, docosahexaenoic acid, arachidonic acid, which can be used alone or in a mixture.

As radical $R_{a11}$ it is likewise possible to use the alkyl radical derived from polycondensation products of hydroxyfunctionalized acids, such as poly-12-hydroxystearic acid or polyricinoleic acid.

Another embodiment of the invention are compounds of the general formula I wherein n and p are 0,
W is hydrogen,
m is a number selected from the groups consisting of 1 to 28, 1 to 4, and 1,
o is a number selected from the groups consisting of 1 to 100 and 1,
q is 1,
$R_a$ is $R_{a1}=R_{a11}$ or $R_a=R_{a2}$, where $R_{a11}$ and $R_{a2}$ are defined as above.

In accordance with the invention it is likewise preferred to use esters of the general formula I where
n and o are 0,
W is hydrogen,
m is a number selected from the groups consisting of 1 to 28, 1 to 4, and 1,
B is —CH$_2$—CH$_2$OH—CH$_2$—O— or —CH$_2$—CH$_2$OR$_b$—CH$_2$—O—,
p is a number selected from the groups consisting of 1 to 20 and 1,
q is 1,
$R_a$ is $R_{a1}=R_{a11}$ or $R_a=R_{a2}$,
where
$R_{a11}$, $R_2$ and $R_b$ are defined as above.

In this context it is possible for the polyglycerol derivatives (p≧2) at least in part to have other linkages of the glycerol units than the 1,3 linkages apparent from formula Ib, of the kind occurring in the typical processes, known from the literature, for obtaining polyglycerols; for example, 1,2 linkages.

Likewise used with preference in accordance with the invention are esters of the general formula I where
n and o are 0,
W is hydrogen,
m is a number selected from the groups consisting of 1 to 28, 1 to 4, and 1,
B is —CH$_2$—CYZ-CH$_2$—O—,
p is q=1,
$R_a$ is $R_{a1}=R_{a11}$ or $R_a=R_{a2}$, where Y, X, $R_{a11}$, and $R_{a2}$ are defined as above.

Likewise used with preference in accordance with the invention are esters of the general formula I where
n is 1,
W is hydrogen or CH$_3$, (in another embodiment of the invention W is hydrogen),
m is a number selected from the groups consisting of 0 to 27 and 1 to 10,
o and p are 0,
$R_a$ is $R_{a1}=R_{a12}$ or $R_a=R_{a2}$, where $R_{a2}$ is defined as above and
$R_{a12}$ is the hydrocarbon radical of a substituted or unsubstituted, optionally branched alcohol having a range of carbon atoms selected from the group consisting of 2 to 30 carbon atoms and having 6 to 22 carbon atoms, which optionally contains one or more multiple bonds, optionally carries hydroxyl groups, optionally carries hydroxyl groups esterified with carboxylic acids or optionally carries amino, alkylamino or dialkylamino groups (in another embodiment of the invention, the alkyl of the alkylamino or dialkylamino groups have 1 to 4 carbon atoms).

Examples of $R_{a12}$ are the hydrocarbon radicals of propanol, butanol, pentanol, hexanol, octanol and also their isomers such as isopropanol, isobutanol, 2-ethylhexanol, isononyl alcohol, isotridecyl alcohol, polyhydric alcohols, such as 1,6-hexanediol, 1,2-pentanediol, dihydroxyacetone, 1,2-propylene glycol, 1,3-propylene glycol, neopentyl glycol, trimethylol propane, pentaerythritol, sorbitol, glycerol, diglycerol, triglycerol, polyglycerol, ethylene glycol, diethylene glycol, triethylene glycol, polyethylene glycol, and also amino-functionalized alcohols, such as N,N-dimethylethanolamine. Further examples are the hydrocarbon radicals of alcohols which are prepared by known processes from monobasic fatty acids based on natural vegetable or animal oils having a range of carbon atoms selected from the group consisting of 6 to 30 carbon atoms and 8 to 22 carbon atoms, such as caproic acid, caprylic acid, capric acid, lauric acid, myristic acid, palmitic acid, palmitoleic acid, isostearic acid, stearic acid, 12-hydroxystearic acid, dihydroxystearic acid, oleic acid, linoleic acid, petroselinic acid, elaidic acid, arachidic acid, behenic acid, erucic acid, and gadoleic acid, which are used alone or in a mixture.

In accordance with the invention the esters of the general formula I are prepared by condensing the corresponding alcohols and acids using at least one enzyme as catalyst. In accordance with the invention it is possible instead of the acids to use the corresponding esters of the carboxylic acids with volatile alcohols for a transesterification; examples of those esters which are suitable are methyl, ethyl or vinyl esters.

The enzymes which can be used in accordance with the invention are those from the group of the hydrolytic enzymes, such as lipases, esterases or proteases, such as cholesterol esterase, esterase from pig liver or lipases from *Candida rugosa*, *Pseudomonas* sp., *Thermomyces langosiosus*, porcine pancreas, *Mucor miehei*, *Alcaligines* sp. In one embodiment of the invention, the enzyme is a lipase such as Lipase B from *Candida antarctica*.

In accordance with the invention it is possible to use whole cells, resting cells, immobilized cells, purified enzymes or cell extracts containing the corresponding enzymes, or mixtures thereof. In accordance with the invention the enzymes can be used in whole-cell systems, in free form or immobilized on suitable supports.

In the process of the invention the reactants are mixed in a suitable reactor (e.g., round-bottomed flask with stirrer, or in a fixed-bed reactor) and heated to the optimum working temperature of the biocatalyst used. In dependence on the biocatalyst used this temperature is selected from the ranges consisting of 20° C. to 100° C. and 35° C. to 80° C. When using a fixed-bed reactor the fixed bed is charged with the selected enzyme and after the reaction temperature has been reached the reaction mixture is pumped through the fixed bed. In the absence of a fixed-bed reactor the enzyme is added directly to the reaction mixture and is isolated by filtration, using suitable devices, after the end of the reaction. In order to achieve conversions as near to completion as possible, the water or low-boiling alcohol formed during the reaction is removed by application of a vacuum or by other suitable techniques, such as by the passage of inert gases (e.g., nitrogen, argon) through the mixture, or the use of absorbents (e.g., molecular sieve).

In accordance with the invention, subsequently, the esters obtained in this way, where appropriate also as a mixture with one another and/or with other, terminally unsaturated organic compounds, examples being allyloxyethanol, glycerol monoallyl ether, allyltrimethylolpropane, α-olefins or terminally unsaturated polyethers, are reacted by known methods by hydrosilylation with an SiH polysiloxane of the general formula II

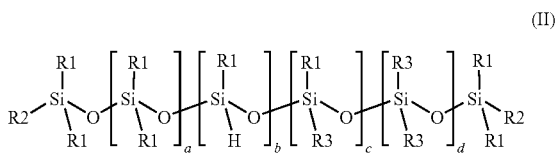

(II)

where
N a+b+c+d+2=3 to 850,
a is 1 to 800,
b is 0 to 400,
c is 0 to 10,
d is 0 to 10, (in one embodiment of the invention:
N a+b+c+d+2=6 to 160,
a is 2 to 150,
b is 2 to 75,
c is 0,
d is 0)

in which the radicals
R1 independently of one another are identical or different and from the following group: saturated or unsaturated, optionally branched alkyl groups having 1 to 30 carbon atoms, alkaryl radicals having 7 to 30 carbon atoms, aryl radicals having 6 to 30 carbon atoms, (in one embodiment of the invention the alkyl groups have 1 to 4 carbon atoms or is methyl and the aryl radical is phenyl),
R2 independently of one another are hydrogen or R1,
R3 independently of one another are identical or different radicals of the general formula IIa

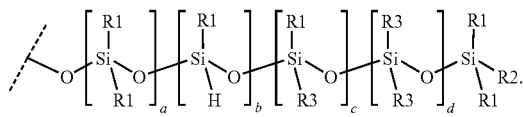

(IIa)

In one embodiment the Si—H-polysiloxane is reacted alone or partly with esters which contain more than one terminal H$_2$C=CH group. These esters correspond to the general formula I in which R$_{a2}$ is described by the formula Id. In this way, organically modified siloxanes are obtained that are of relatively high molecular mass, generally crosslinked.

The skilled worker is familiar with the fact that the compounds are in the form of a mixture having a distribution which is governed essentially by laws of statistics. The values of the indices a, b, c, and d therefore represent average values.

In accordance with the invention the hydrosilylation is carried out by established methods in the presence of a catalyst. In this context it is possible for example to use catalysts typically employed for hydrosilylations, such as complexes of platinum, of rhodium, of osmium, of ruthenium, of palladium or of iridium, or similar compounds, or the corresponding elements alone, or their derivatives immobilized on silica, alumina or activated carbon or similar support materials. With preference the hydrosilylation is carried out in the presence of Pt catalysts such as cis-platin or Karstedt catalyst [tris(divinyltetra-methyldisiloxane)bisplatinum].

The amount of catalyst used is selected from the amount consisting of $10^{-7}$ to $10^{-1}$ mol per mole of olefin and 1 to 20 ppm. The hydrosilylation is carried out at temperatures selected from group consisting of between 0 and 200° C. and between 50 and 140° C. Solvents are generally not necessary for the implementation of the reaction. The reaction can, however, be carried out in suitable solvents such as aliphatic or aromatic hydrocarbons, cyclic oligosiloxanes, alcohols or esters.

The invention further provides compounds of the formula I where n=p=0, W=X=hydrogen, m=o=q=1, and R$_a$=R$_{a13}$. R$_{a13}$ is the alkyl radical of mono-basic fatty acids based on natural vegetable or animal oils having 8 to 16 carbon atoms, which may be present alone or in a mixture. In accordance with the invention R$_{a13}$ can also be the alkyl radical of isononanoic acid (3,5,5-trimethylhexanoic acid), 2-ethylhexanoic acid, ricinoleic acid, 12-hydroxystearic acid, polyricinoleic acid or poly-12-hydroxystearic acid.

The invention further provides compounds of the formula I where n=p=0, W=hydrogen, X=hydrogen or methyl, (in one embodiment of the invention x is hydrogen), m=q=1, o=2 to 100, (in one embodiment of the invention o=3 to 100) and R$_a$=R$_{a14}$. R$_{a14}$ is the alkyl radical of commercially customary acids having 4 to 30 carbon atoms, such as butanoic acid or pentanoic acid, for example, and also the alkyl radicals of mono-basic fatty acids based on natural vegetable or animal oils having carbon number from a range selected from the group consisting of 6 to 30 carbon atoms and 8 to 22 carbon atoms, such as caproic acid, caprylic acid, capric acid, lauric acid, myristic acid, palmitic acid, palmitoleic acid, isostearic acid, stearic acid, 12-hydroxystearic acid, dihydroxystearic acid, oleic acid, linoleic acid, petroselenic acid, elaidic acid, arachidic acid, behenic acid, erucic acid, gadoleic acid, linolenic acid, eicosapentaenoic acid, docosahexaenoic acid and arachidonic acid, which can be used alone or in a mixture. The radical R$_{a14}$ may likewise be the alkyl radical of polycondensation products of hydroxy-functionalized acids, such as poly-12-hydroxystearic acid or polyricinoleic acid, for example.

The invention further provides compounds of the formula I where n=o=p=0, q=1, W=hydrogen, m=2 to 4, (in another embodiment of the invention m=4) and R$_a$=R$_{a14}$. R$_{a14}$ here is defined as above.

The invention further provides compounds of the formula I where n=o=0, W=hydrogen, m=p=q=1, B=—CH$_2$—CH$_2$OH—CH$_2$—O—, and R$_a$=R$_{a15}$. R$_{a15}$ is the alkyl radical of myristic acid or coconut fatty acid.

The invention further provides siloxane compounds of the general formula III,

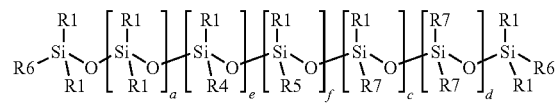

(III)

where
N a+b+c+d+e+f+2=3 to 850,
a is 1 to 800,
c is 0 to 10,
d is 0 to 10,
e is 0 to 400, and
f is 0 to 400, (in one embodiment of the invention:
N a+b+c+d+e+f+2=6 to 160,
a is 2 to 150,
c is 0, d is 0,
e is 2 to 75, and
f is 0 to 75)

in which case the radicals
R1 independently of one another are identical or different and from the group of saturated or unsaturated, optionally branched alkyl groups having 1 to 30 carbon atoms, alkaryl radicals having 7 to 30 carbon atoms, aryl radicals having 6 to 30 carbon atoms, (in one embodiment of the invention the alkyl groups have 1 to 4 carbon atoms or is methyl and the aryl radical is phenyl),
R4 independently of one another are identical or different ester radicals of the general formula IIIa

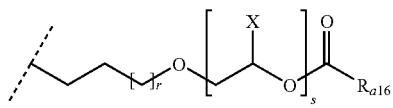
(IIIa)

with
r being 3 and
s being 0 or
r being 1 and
s being 1 to 100, (in another embodiment of the invention s is 1)
X independently at each occurrence being identical or different radicals from the group —H, —CH$_3$, —CH$_2$CH$_3$ or phenyl, (in another embodiment of the invention X is hydrogen), and
R$_{a16}$ being the alkyl radicals of mono-basic fatty acids based on natural vegetable or animal oils having carbon number from a range selected from the group consisting of 6 to 30 carbon atoms and 8 to 22 carbon atoms, such as caproic acid, caprylic acid, capric acid, lauric acid, myristic acid, palmitic acid, palmitoleic acid, isostearic acid, stearic acid, 12-hydroxystearic acid, dihydroxystearic acid, oleic acid, linoleic acid, petroselenic acid, elaidic acid, arachidic acid, behenic acid, erucic acid, gadoleic acid, linolenic acid, eicosapentaenoic acid, docosahexaenoic acid or arachidonic acid, which may be present alone or in a mixture. The radical R$_{a16}$ may likewise be the alkyl radical of polycondensation products of hydroxy-functionalized acids, such as poly-12-hydroxy-stearic acid or polyricinoleic acid, for example;

and additionally the radicals
R5 independently at each occurrence being saturated or unsaturated, optionally branched alkyl groups having 1 to 30 carbon atoms or alkaryl radicals having 7 to 30 carbon atoms, (in one embodiment of the invention the alkyl groups have 6 to 22 carbon atoms), or
R5 are the radicals of the general formula IIIb

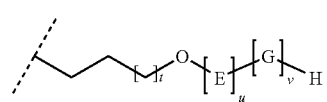
(IIIb)

with
t being 1 to 28,
u being 1 to 100,
E being an oxyalkenyl radical of the general formula Ia,

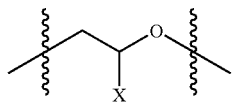
(Ia)

with
X radicals independently being identical or different radicals from the group —H, —CH$_3$, —CH$_2$CH$_3$ or -phenyl, (in another embodiment of the invention X is hydrogen),
v being 0 to 20,
G if v=1 being a glycerol-derived oxyalkenyl radical of the general formula Ib,

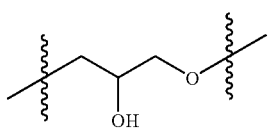
(Ib)

or G being the radical of the general formula Ic

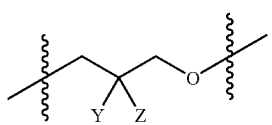
(Ic)

with
Y and Z independently of one another being identical or different radicals from the group —H, —CH$_3$, —CH$_2$CH$_3$ or —CH$_2$OH, or
G if v≧2 being a polyglycerol radical formed from monomers of glycerol and optionally esterified with R$_b$,
R$_b$ is defined as above,
R6 independently at each occurrence being R1, R4 or R5, where R1, R4 and R5 are defined as above and R6 being the same as R4 if e=0,
R7 independently at each occurrence being identical or different radicals of the general formula IIIc

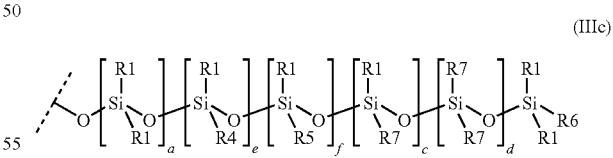
(IIIc)

where
R1, R4, R5 and R6 are defined as above.
Radicals according to the general formula IIIb may in also be compounds where
t is a number selected from the group consisting of 1 to 28 and 1, and
u is a number selected from the group consisting of 1 to 100, 1 to 20, and 1, and
v is 0, or t is a number selected from the group consisting of 1 to 28 and 1, and u is 0, and v is a number selected from the group consisting of 1 to 20, 1 to 6, and 1.

Examples 1, 2, 11, and 12 below are not inventive but instead illustrate the state of the art. Examples 3 to 10 and 13 to 20 describe the process for preparing the compounds of the invention and also their properties in more detail. The examples serve to illustrate the process and are not in any way intended to restrict the scope of application of the invention. Results of analytical methods such as $^1$H, $^{13}$C and $^{29}$Si-NMR and GPC are in accordance with the stated structures of the products.

The invention is further described by the following non-limiting examples which further illustrate the invention, and are not intended, nor should they be interpreted to, limit the scope of the invention.

EXAMPLES

Example 1

PTSA-catalyzed synthesis of coconut fatty acid 1-allylglyceryl ester

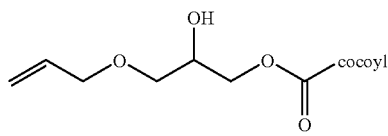

(IV)

A multi-necked round-bottom flask is charged with 185.1 g of 1-allylglycerol and 213.4 g of coconut fatty acid. Following the addition of 0.4 g of para-toluenesulfonic acid (PTSA) this initial charge is heated to 170° C. under a nitrogen atmosphere. After 7 hours the reaction mixture is cooled, the catalyst is neutralized with 1.51 g of a $K_2CO_3$ solution (50% in water), the water is distilled off under reduced pressure, and solids are removed by filtration. The filtrate yields 379 g of the product without further workup, as a light-brown liquid.

Example 2

Tin(II) oxalate-catalyzed synthesis of coconut fatty acid 1-allylglyceryl ester

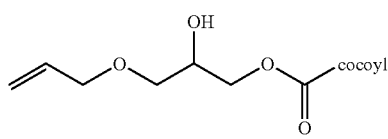

(IV)

A multi-necked round-bottom flask is charged with 185.1 g of 1-allylglycerol and 213.4 g of coconut fatty acid. Following the addition of 0.7 g of tin(II) oxalate this initial charge is heated to 220° C. After 4 hours the reaction mixture is cooled and the catalyst is filtered off using 2.4 g of Tinex P (Goldschmidt TIB, Mannheim). The filtrate yields 370 g of the product without further workup, as a light-brown liquid.

Example 3

Enzymatic synthesis of coconut fatty acid 1-allylglyceryl ester

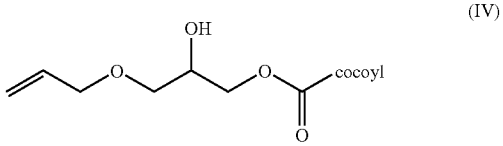

(IV)

A multi-necked round-bottom flask is charged with 185.1 g of 1-allylglycerol and 213.4 g of coconut fatty acid, and this initial charge is heated to 50° C. Following the addition of 19 g of Novozym 435 (immobilized lipase B from *C. antarctica*, purchased from Novozymes A/S, Bagsvaerd, Denmark) reduced pressure is applied (20 mbar) and the water of reaction is removed by distillation. After 7 hours the immobilized enzyme is removed by filtration. The filtrate yields 379 g of the product without further workup, as a colorless liquid.

Example 4

Enzymatic synthesis of stearic acid 1-allylglyceryl ester

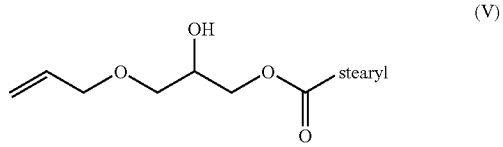

(V)

A multi-necked round-bottom flask is charged with 158.6 g of 1-allylglycerol and 237 g of stearic acid, and this initial charge is heated to 60° C. Following the addition of 19 g of Lipozym RM 1M (immobilized lipase from *Mucor miehei*, Novozymes A/S) reduced pressure is applied (20 mbar) and the water of reaction is removed by distillation. After 48 hours the immobilized enzyme is removed by filtration. The filtrate yields 382 g of the product without further workup, as a colorless liquid.

Example 5

Enzymatic synthesis of coconut fatty acid allyloxyethanol ester

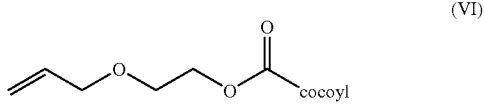

(VI)

A multi-necked round-bottom flask is charged with 134.8 g of allyloxyethanol and 243.9 g of coconut fatty acid, and this initial charge is heated to 40° C. Following the addition of 18 g of Novozym 435 reduced pressure is applied (20 mbar) and the water of reaction is removed by distillation. After 10 hours the immobilized enzyme is removed by filtration. The filtrate yields 344 g of the product without further workup, as a colorless liquid.

Example 6

Enzymatic synthesis of coconut fatty acid hexenyl ester

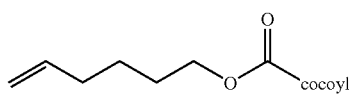
(VII)

A multi-necked round-bottom flask is charged with 140.0 g of hex-5-en-1-ol and 258.1 g of coconut fatty acid, and this initial charge is heated to 60° C. Following the addition of 19 g of Novozym 435 reduced pressure is applied (20 mbar) and the water of reaction is removed by distillation. After 7 hours the immobilized enzyme is removed by filtration. The filtrate yields 360 g of the product without further workup, as a colorless liquid.

Example 7

Enzymatic synthesis of undecylenic acid octyl ester

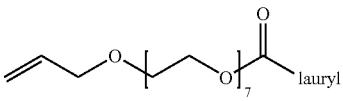
(VIII)

A multi-necked round-bottom flask is charged with 82 g of 1-octanol and 124.9 g of methyl-10-undecylenate, and this initial charge is heated to 60° C. Following the addition of 10 g of Novozym 435 reduced pressure is applied (20 mbar) and the methanol released is removed by distillation. After 6 hours the immobilized enzyme is removed by filtration. The filtrate yields 186 g of the product without further workup, as a colorless liquid.

Example 8

1,6-hexanediol diundecylenate

A multi-necked round-bottom flask is charged with 44.9 g of 1,6-hexanediol and 150.7 g of methyl-10-undecylenate, and this initial charge is heated to 60° C. Following the addition of 9.8 g of Novozym 435 reduced pressure is applied (20 mbar) and the methanol released is removed by distillation. After 6 hours the immobilized enzyme is removed by filtration. The filtrate yields 171 g of the product without further workup, as a colorless liquid.

Example 9

Diallyloxyethyl adipate

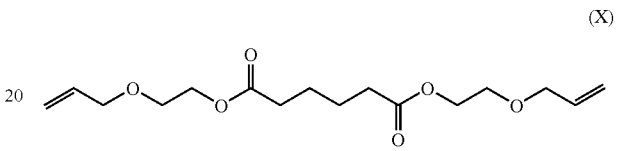
(X)

A multi-necked round-bottom flask is charged with 125.6 g of adipic acid and 210.7 g of allyloxyethanol, and this initial charge is heated to 60° C. Following the addition of 15.9 g of Novozym 435 reduced pressure is applied (20 mbar) and the water released is removed by distillation. After 8 hours the immobilized enzyme is removed by filtration. The filtrate yields 270 g of the product without further workup, as a colorless liquid.

Example 10

Allylpolyethylene glycol-7 laurate

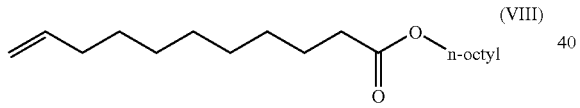
(XI)

A multi-necked round-bottom flask is charged with 200.4 g of allylpolyethylene glycol-7 and 100.2 g of lauric acid, and this initial charge is heated to 60° C. Following the addition of 15 g of Novozym 435 reduced pressure is applied (20 mbar) and the water released is removed by distillation. After 8 hours the immobilized enzyme is removed by filtration. The filtrate yields 291 g of the product without further workup, as a colorless liquid.

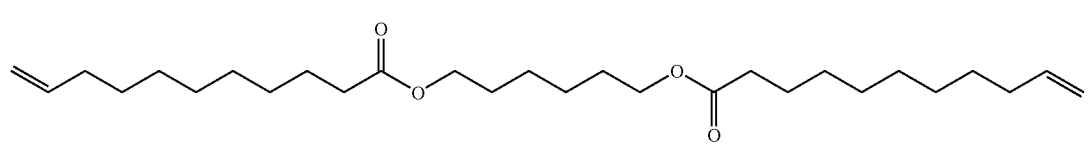
(IX)

Example 11, not Inventive (Comparative Example)

Hydrosilylation of the reaction product of Example 1 in order to prepare a polysiloxane of the general formula XII:

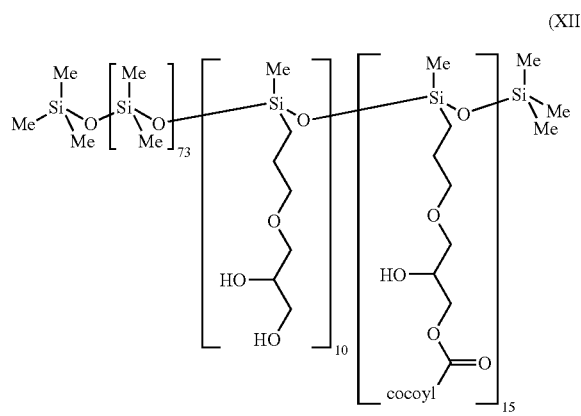

(XII)

A four-necked flask with stirrer, dropping funnel, thermometer, and reflux condenser is charged with 8.5 g (64 mmol) of glycerol monoallyl ether, 31.5 g (96 mmol) of the coconut fatty acid glycerol monoallyl ether ester from Example 1, and 10 ppm of Karstedt catalyst. This initial charge is heated to 95° C. 34.1 g (123 mmol of SiH) of an SiH-siloxane of the general formula XIII:

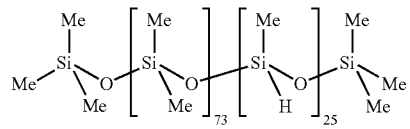

(XIII)

are added dropwise and the batch is stirred at 95° C. The batch very rapidly becomes a gel, whereupon the reaction is terminated.

Example 12, not Inventive (Comparative Example)

Hydrosilylation of the reaction product of Example 2 in order to prepare a polysiloxane of the general formula XII:

A four-necked flask with stirrer, dropping funnel, thermometer, and reflux condenser is charged with 8.5 g (64 mmol) of glycerol monoallyl ether, 31.5 g (96 mmol) of the coconut fatty acid glycerol monoallyl ether ester from Example 2, and 10 ppm of Karstedt catalyst. This initial charge is heated to 95° C. 34.1 g (123 mmol of SiH) of an SiH-siloxane of the general formula XIII are added dropwise and the batch is stirred at 95° C. The batch very rapidly becomes a gel, whereupon the reaction is terminated.

Example 13

Hydrosilylation of the Reaction Product of Example 3

Preparation of a Polysiloxane of the General Formula XII

A four-necked flask with stirrer, dropping funnel, thermometer, and reflux condenser is charged with 8.5 g (64 mmol) of glycerol monoallyl ether, 31.5 g (96 mmol) of the coconut fatty acid glycerol monoallyl ether ester from Example 3, and 10 ppm of Karstedt catalyst. This initial charge is heated to 95° C. 34.1 g (123 mmol of SiH) of an SiH-siloxane of the general formula XIII are added dropwise and the batch is stirred at 95° C. for 1 h. According to SiH value determination, complete conversion of the SiH-siloxane is obtained. Volatile fractions are subsequently distilled off under reduced pressure at 110° C. This gives a viscous, slightly turbid, pale yellow product.

Example 14

Hydrosilylation of the Reaction Product of Example 4

Preparation of an Inventive Polysiloxane of the General Formula XIV

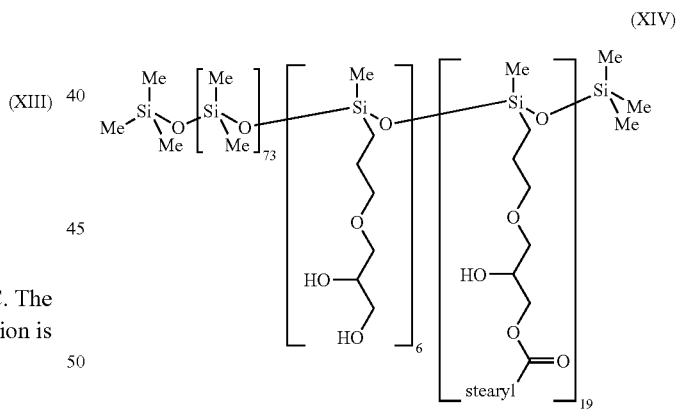

(XIV)

A four-necked flask with stirrer, dropping funnel, thermometer, and reflux condenser is charged with 20.6 g (156 mmol) of glycerol monoallyl ether, 203.9 g (494 mmol) of the stearic acid glycerol monoallyl ether ester from Example 4, and 10 ppm of Karstedt catalyst. This initial charge is heated to 90° C. 142.5 g (500 mmol of SiH) of an SiH-siloxane of the general formula XIII are added dropwise and the batch is stirred at 90° C. for 1.5 h. According to SiH value determination, complete conversion of the SiH-siloxane is obtained. Volatile fractions are subsequently distilled off under reduced pressure at 100° C. This gives a bright yellow waxlike solid product.

Example 15

Hydrosilylation of the Reaction Product Of Example 5

Preparation of an Inventive Polysiloxane Of The General Formula XV:

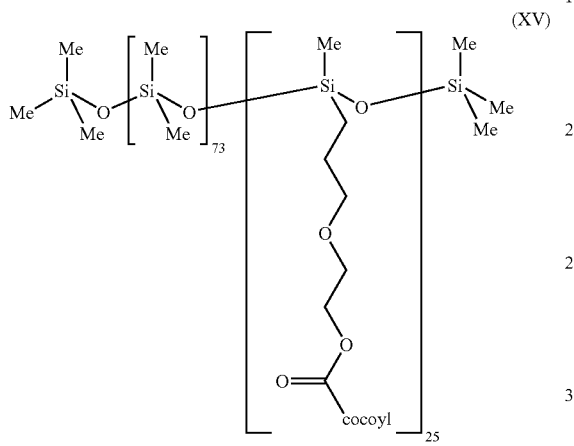

(XV)

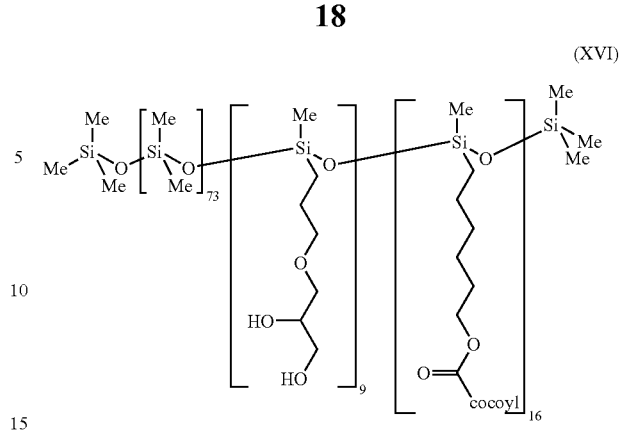

(XVI)

A four-necked flask with stirrer, dropping funnel, thermometer, and reflux condenser is charged with 6.2 g (47 mmol) of glycerol monoallyl ether, 23.6 g (83 mmol) of the coconut fatty acid hex-5-en-1-ol ester from Example 6, and 10 ppm of Karstedt catalyst. This initial charge is heated to 95° C. 28.9 g (100 mmol of SiH) of an SiH-siloxane of the general formula XIII are added dropwise and the batch is stirred at 95° C. for 1 h. According to SiH value determination, complete conversion of the SiH-siloxane is obtained. Volatile fractions are subsequently distilled off under reduced pressure at 110° C. This gives a viscous, slightly turbid, virtually colorless product.

Example 17

Hydrosilylation of the Reaction Product of Example 7

Preparation of an Inventive Polysiloxane of the General Formula XVII:

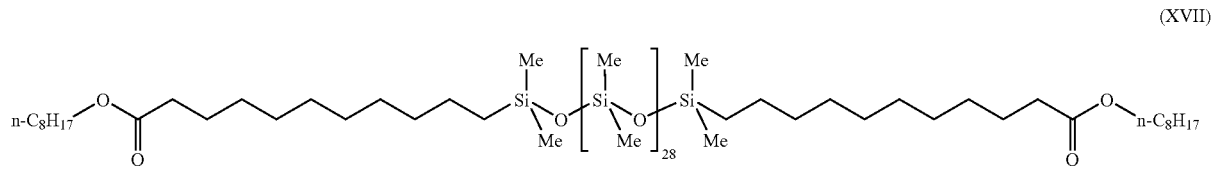

(XVII)

A four-necked flask with stirrer, dropping funnel, thermometer, and reflux condenser is charged with 29.1 g (100 mmol) of the coconut fatty acid allyloxyethanol ester from Example 5, and 10 ppm of Karstedt catalyst. This initial charge is heated to 95° C. 22.2 g (77 mmol of SiH) of an SiH-siloxane of the general formula XIII are added dropwise and the batch is stirred at 95° C. for 1 h. According to SiH value determination, complete conversion of the SiH-siloxane is obtained. Volatile fractions are subsequently distilled off under reduced pressure at 110° C. This gives a slightly viscous, pale yellow product.

A four-necked flask with stirrer, dropping funnel, thermometer, and reflux condenser is charged with 19.2 g (65 mmol) of the undecylenic acid octyl ester from Example 7, and 10 ppm of Karstedt catalyst. This initial charge is heated to 95° C. 57.2 g (50 mmol of SiH) of an SiH-siloxane of the general formula XVIII:

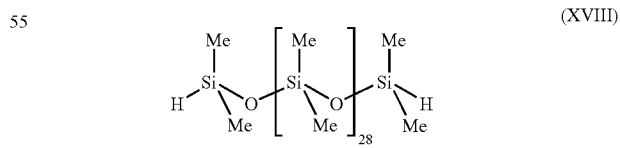

(XVIII)

are added dropwise and the batch is stirred at 95° C. for 2 h. According to SiH value determination, complete conversion of the SiH-siloxane is obtained. Volatile fractions are subsequently distilled off under reduced pressure at 110° C. This gives a clear, virtually colorless liquid.

Example 16

Hydrosilylation of the Reaction Product of Example 6

Preparation of an Inventive Polysiloxane of the General Formula XVI:

Example 18
Hydrosilylation of the Reaction Product of Example 8

Preparation of an Inventive Polysiloxane Copolymer of the General Formula XIX:

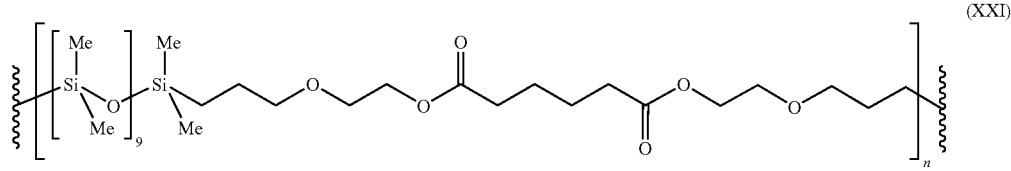

(XIX)

A four-necked flask with stirrer, dropping funnel, thermometer, and ref lux condenser is charged with 41.2 g (91 mmol) of the undecylenic acid 1-6-hexanediol diester from Example 8, and 15 ppm of cis-platin catalyst. This initial charge is heated to 120° C. 46.6 g (140 mmol of SiH) of an SiH-siloxane of the general formula XX:

(XX)

are added dropwise over the course of 10 minutes and the batch is stirred at 120° C. for 1 h. According to SiH value determination, complete conversion of the SiH-siloxane is obtained. This gives a slightly opaque, slightly yellow oil.

Molar weight distribution according to GPC: $M_w=12319$, $M_n=4672$.

Example 19
Hydrosilylation of the Reaction Product of Example 9

Preparation of an Inventive Polysiloxane Copolymer of the General Formula XXI:

(XXI)

A four-necked flask with stirrer, dropping funnel, thermometer, and reflux condenser is charged with 40.7 g (130 mmol) of the adipic acid allyloxyethanol diester from Example 9, and 5 ppm of cis-platin catalyst. This initial charge is heated to 95° C. 66.6 g (200 mmol of SiH) of an SiH-siloxane of the general formula XX are added dropwise over the course of 10 minutes and the batch is stirred at 95° C. for 1 h. According to SiH value determination, complete conversion of the SiH-siloxane is obtained. This gives a slightly opaque, slightly yellow oil.

Molar weight distribution according to GPC: $M_w=8633$, $M_n=3265$.

Example 20
Hydrosilylation of the Reaction Product of Example 10

Preparation of an Inventive Polysiloxane of the General Formula XXII:

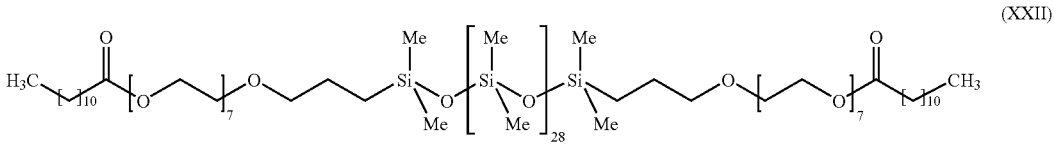

(XXII)

A four-necked flask with stirrer, dropping funnel, thermometer, and reflux condenser is charged with 57.1 g (50 mmol of SiH) of an SiH-siloxane of the general formula XVIII, and 10 ppm of Karstedt catalyst. This initial charge is heated to 90° C. 38.4 g (130 mmol) of the allyl polyether laurate from Example 10 are added dropwise over the course of 10 minutes and the batch is stirred at 90° C. for 1 h. According to SiH value determination, complete conversion of the SiH-siloxane is obtained. This gives a slightly opaque, virtually colorless liquid.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:

1. A process for preparing siloxanes modified with organic esters, by hydrosilylating siloxanes with terminally unsaturated esters, which comprises preparing the terminally unsaturated esters used using at least one enzyme as catalyst.

2. The process as claimed in claim 1, wherein terminally unsaturated esters used are compounds of the general formula I

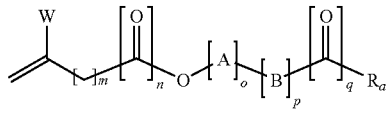 (I)

where
W is hydrogen or methyl,
m is 0 to 28,
n is 0 or 1,
o is 0 to 100,
A is an oxyalkenyl radical of the general formula Ia

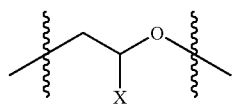 (Ia)

where
X radicals independently are identical or different radicals from the group —H, —CH$_3$, —CH$_2$CH$_3$ or -phenyl,
p is from 0 to 20,
B if p=1 is a glycerol-derived oxyalkenyl radical, optionally esterified with R$_b$, of the general formula Ib

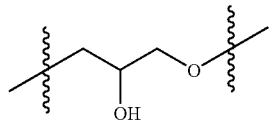 (Ib)

where
R$_b$ is the acyl radical of linear, branched, saturated or unsaturated carboxylic acids having 2 to 30 carbon atoms and optionally carrying additional hydroxyl groups, or
B if p=1 is the radical of the general formula Ic

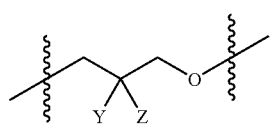 (Ic)

where
Y and Z independently of one another are identical or different radicals from the group —H, —CH$_3$, —CH$_2$CH$_3$, —CH$_2$OH or —CH$_2$OR$_b$,
where
R$_b$ is defined as above, or
B if p≧2 is a polyglycerol radical formed from monomers of glycerol and optionally esterified with R$_b$,
R$_b$ is defined as above,
R$_a$ is hydrogen, R$_{a1}$ or R$_{a2}$,
where
R$_{a1}$ is a linear or branched, saturated or unsaturated alkyl radical having 1 to 200 carbon atoms which optionally carries hydroxyl groups, optionally carries hydroxyl groups esterified with carboxylic acids and optionally carries amino, alkylamino or dialkylamino groups,
R$_{a2}$ is a radical of the general formula Id

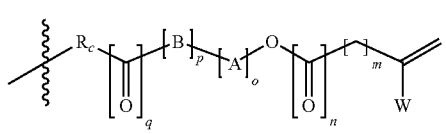 (Id)

and
R$_c$ is a saturated or unsaturated difunctional hydrocarbon radical having 2 to 20 carbon atoms,
where
q=0 or 1 provided that n+q=1, and
if R$_a$ is hydrogen, then q is 0 and o+p≧1.

3. The process as claimed in claim 2, wherein esters of the general formula I are used
where
n, o and p are 0,
W is hydrogen,
m is 1 to 28,
q is 1,
R$_a$, R$_{a1}$=R$_{a11}$ or R$_a$=R$_{a2}$,
where
R$_{a2}$ is defined as in claim 2 and
R$_{a11}$ is the alkyl radical derived from commercially customary acids, such as acetic acid, propanoic acid, butanoic acid, pentanoic acid, chloroacetic acid, trifluoroacetic acid, ethylhexanoic acid, isononanoic acid, isotridecanoic acid or isostearic acid, or the alkyl radical derived from mono-basic fatty acids based on natural vegetable or animal oils having 6 to 30 carbon atoms, in particular having 8 to 22 carbon atoms, such as caproic acid, caprylic acid, capric acid, lauric acid, myristic acid, palmitic acid, palmitoleic acid, isostearic acid, stearic acid, 12-hydroxystearic acid, dihydroxystearic acid, oleic acid, linoleic acid, petroselenic acid, elaidic acid, arachidic acid, behenic acid, erucic acid, gadoleic acid, linolenic acid, eicosapentaenoic acid, docosahexaenoic acid, arachidonic acid, which can be used alone or in a mixture, or the alkyl radical derived from poly-condensation products of hydroxy-functionalized acids, such as poly-12-hydroxystearic acid or polyricinoleic acid.

4. The process as claimed in claim 2, wherein esters of the general formula I are used
where
n and p are 0,
W is hydrogen,
m is 1 to 28,
o is 1 to 100,
q is 1,
R$_a$ is R$_{a1}$=R$_{a11}$ or R$_a$=R$_{a2}$, where R$_{a11}$ is defined as in claim 3.

5. The process as claimed in claim 2, wherein esters of the general formula I are used
where
n and o are 0,
W is hydrogen,
m is 1 to 28,
B is —CH$_2$—CH$_2$OH—CH$_2$—O— or —CH$_2$—CH$_2$OR$_b$—CH$_2$—O—, where R$_b$ is defined as in claim 2, p is 1 to 20,
q is 1,
$R_a$ is $R_{a1}=R_{a11}$ or $R_a=R_{a2}$, where $R_{a11}$ is defined as in claim 3.

6. The process as claimed in claim 2, wherein esters of the general formula I are used
where
n and o are 0,
W is hydrogen,
m is 1 to 28,
B is —$CH_2$—CYZ-$CH_2$—O—,
where Y and Z are defined as in claim 2,
p is q=1,
$R_a$ is $R_{a1}=R_{a11}$ or $R_a=R_{a2}$,
where
$R_{a11}$ is defined as in claim 3.

7. The process as claimed in claim 2, wherein esters of the general formula I are used
where
n is 1,
W is hydrogen or $CH_3$,
m is 0 to 27,
o and p are 0,
$R_a$ is $R_{a1}=R_{a12}$ or $R_a=R_{a2}$,
where
$R_{a12}$ is the hydrocarbon radical of a substituted or unsubstituted, optionally branched alcohol having 2 to 30 carbon atoms, preferably having 6 to 22 carbon atoms, which optionally contains one or more multiple bonds, optionally carries hydroxyl groups, optionally carries hydroxyl groups esterified with carboxylic acids or optionally carries amino, alkylamino or dialkylamino groups.

8. The process as claimed in claim 1, wherein the esters are prepared using the corresponding esters of volatile alcohols for a transesterification, and are selected from the group consisting of methyl, ethyl, and vinyl esters.

9. The process as claimed in claim 1, wherein the at least one enzyme is selected from the group consisting of lipases, esterases, proteases, and lipase B from *Candida antarctica*.

10. The process as claimed in claim 1, wherein as SiH-polysiloxane a compound of the general formula II

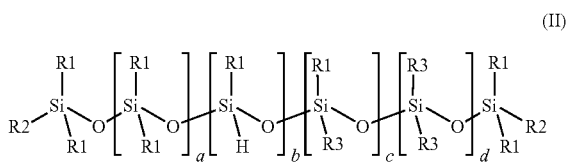

(II)

is used where
N a+b+c+d+2=3 to 850,
a is 1 to 800,
b is 0 to 400,
c is 0 to 10,
d is 0 to 10, and
in which the radicals
R1 independently of one another are identical or different and from the following group: saturated or unsaturated, optionally branched alkyl groups having 1 to 30 carbon atoms, alkaryl radicals having 7 to 30 carbon atoms, aryl radicals having 6 to 30 carbon atoms, R2 independently of one another are hydrogen or R1,
R3 independently of one another are identical or different radicals of the general formula IIa.

11. The process as claimed in claim 10, wherein as SiH-polysiloxane a compound of the general formula II

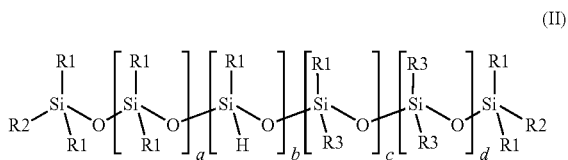

(II)

is used where
N a+b+c+d+2=6 to 160,
a is 2 to 150,
b is 2 to 75,
c is 0,
d is 0, and in which the radicals
R1 independently of one another an alkyl groups having 1 to 4 carbon atoms or phenyl,
R2 independently of one another are hydrogen or R1,
R3 independently of one another are identical or different radicals of the general formula IIa.

* * * * *